United States Patent [19]

Knoll et al.

[11] 4,162,327

[45] Jul. 24, 1979

[54] N,N-DISUBSTITUTED-2-FURYLETHYL AMINES

[75] Inventors: József Knoll; Zoltán Ecsery; Judit Hermann née Vörös; Zoltán Török; Éva Somfai, all of Budapest; Gábor Bernáth, Szeged, all of Hungary

[73] Assignee: Chinoin Gyogysler Es Vegyeszeti Termeken Gyara Rt., Budapest, Hungary

[21] Appl. No.: 754,278

[22] Filed: Dec. 27, 1976

[30] Foreign Application Priority Data

Dec. 29, 1975 [HU] Hungary ............................ OE 1632

[51] Int. Cl.$^2$ ..................... A61K 31/34; C07D 307/52
[52] U.S. Cl. .................... 424/285; 260/347.7
[58] Field of Search ...................... 260/347.7; 424/285

[56] References Cited

U.S. PATENT DOCUMENTS

| 2,847,271 | 8/1958 | Siclari et al. | 260/347.7 X |
| 3,211,741 | 10/1965 | Martin et al. | 260/347.7 X |
| 3,366,688 | 1/1968 | Hargrove | 260/347.7 X |
| 3,639,476 | 2/1972 | Eberle et al. | 260/347.7 X |

OTHER PUBLICATIONS

Novitskii et al., Chemical Abstracts, vol. 62 (1965), 569b.

Primary Examiner—Richard Raymond
Attorney, Agent, or Firm—Karl F. Ross

[57] ABSTRACT

A compound of the formula

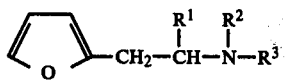

or a pharmaceutically effective salt thereof in which $R^1$ and $R^2$ are hydrogen or lower alkyl and $R^3$ is halogenoalkenyl or propinyl. The compounds have pharmacological effects similar to those of phenylethylamine but are free from the amphetamine effect with an excellent therapeutic index and selectivity especially with respect to inhibition of monoaminooxidase.

8 Claims, No Drawings

N,N-DISUBSTITUTED-2-FURYLETHYL AMINES

This invention relates to new amines. More particularly it is concerned with new N-2-(2-furyl)-ethyl-amine derivatives compositions comprising the same.

According to an aspect of the present invention there are provided compounds of the formula I

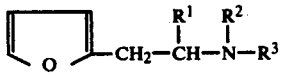 (I)

and salts thereof (wherein $R^1$ and $R^2$ are hydrogen or lower alkyl, and $R^3$ is halogenoalkenyl or propynyl).

It is known that furyl-ethyl amines exhibit a pharmacological effect similar to that of phenyl-ethyl amine [J. Pharmacol. 72, 265 (1941)]. The new compounds of the formula I are free of the undesired "amphetamine" effect, but are capable of selective inhibition of monoaminooxidase. Some known compounds of different chemical structure are described to have selective monoaminooxidase inhibiting effect. (Biochemical Pharmacology 18, (1969) 1447; Br. J. Pharmacology 45, (1972) 490). The said compounds inhibit however mainly the oxidation of 5-hydroxy-tryptamine. It is known that N-alpha-dimethyl-N-beta-phenyl-N-propynylamine (British Pat. No. 1,031,425) inhibits the oxidation of benzyl amine (Br. J. Pharmacology 45, 490 (1972)). The compounds of the formula I possess however more favorable properties than the phenyl-ethyl-propynyl amine derivatives mentioned above.

The compounds of the formula I possess a chiral carbon atom and may be present either in racemic or in optically active forms. The present invention encompasses both the racemic and optically active forms of the compounds of the formula I and the preparation thereof.

The term "lower alkyl group" means straight or branched chain alkyl groups having 1–4 carbon atoms (e.g. methyl, ethyl, n-propyl, isopropyl, n-butyl, isobutyl, etc.) The alkyl group preferably can be a methyl group. The halogenoalkenyl group can comprise 2 or 3 carbon atoms and preferably chlorine or bromine as halogen (e.g. bromopropenyl).

The salts of the compounds of the formula I may be formed with inorganic or organic acids (e.g. hydrochloric acid, hydrobromic acid, sulfuric acid, phosphoric acid, maleic acid, tartaric acid, fumaric acid, succinic acid, lactic acid, etc.).

According to a further aspect of the present invention there is provided a process for the preparation of compounds of the formula I

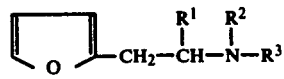 (I)

which comprises (a) reacting a compound of the formula

 (II)

with a compound of the formula III $B-R^3$ (III)

(wherein A and B stand for groups, which on reacting with each other are capable of the formation of the bivalent

radical) and if desired converting a halogeno alkenyl group in the obtained product into a propynyl group; or (b) condensing a compound of the formula IV

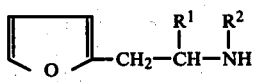 (IV)

with formaldehyde and acetylene and if desired converting a compound of the formula I thus obtained into its acid addition salt or setting free a compound of the formula I from its acid addition salt and if desired separating a racemic compound of the formula I into its optically active isomers.

According to an embodiment of method (a) of our process a compound of the formula IV is reacted with a compound of the formula III, wherein $R^3$ is propargyl and B is halogen or a sulfonic acid ester group, e.g. an alkylsulfonyloxy or arylsulfonyloxy group, such as chlorine, bromine, benzenesulfonyloxy, p-toluenesulfonyloxy or methanesulfonyloxy. The reaction may be carried out in a solvent or without solvent. It is preferred to add an acid binding agent to the reaction mixture. As the acid binding agent, inorganic or organic bases, such as alkali or alkali earth metal hydroxides, carbonates or tertiary amines can be used. An excess of the amine of the formula IV can also serve as acid binding agent. In this case it is preferred to use the excess of amine both as acid binding agent and reaction medium. The reaction may be accomplished preferably at a temperature between 20° and 120° C. As solvent aliphatic and aromatic hydrocarbons, such as gasoline, benzene and its homologues, alkanols (e.g. ethanol, methanol, butanol, etc.) ketones (e.g. methyl-ethyl-ketone, cyclohexanone, etc.) can be used. According to a particularly preferred embodiment of this reaction variant an amine of the formula IV is dissolved in toluene and propargyl bromide and an aqueous sodium hydroxide solution are added simultaneously dropwise. The reaction is completed by heating if necessary.

The product is recovered from the reaction mixture by addition of an alkali and subsequent extraction. If the reaction is carried out in a water-immiscible solvent, it is preferred to remove this solvent by distillation and adding the aqueous sodium hydroxide to the residue. The two-phase mixture is extracted with a water-immiscible solvent (e.g. ether or benzene), the extract is dried, evaporated and the residue is purified by fractionated distillation.

If the compound of the formula I thus obtained is a tertiary base ($R^2$ is alkyl) the product may be advantageously purified by the acylation of the evaporation residue. In this case the unreacted starting material of the formula IV (secondary base) is acylated, the acylated product thus obtained is insoluble in diluted acids and the tertiary base of the formula I can be recovered by extraction with diluted acid in pure form. Acylation may be carried out with conventional acylating agents (e.g. acid anhydrides or acid chlorides such as acetic anhydride or benzoyl chloride) in the presence of an alkali. After acylation the reaction mixture is extracted with cold diluted hydrochloric acid, whereupon the acidic extract is made alkaline, the precipitated tertiary amine of the formula I is extracted with a solvent, dried, evaporated and the residue is distilled off. The product may be converted into a salt formed with an organic or inorganic acid.

According to an other embodiment of process (a) a compound of the formula IV is reacted with propargyl aldehyde under simultaneous or subsequent reduction. One may proceed by reacting the compound of the formula IV with propargyl aldehyde in a solvent or without solvent. As reaction medium preferably water-immiscible solvents (e.g. benzene and its homologues, such as toluene, xylene, petrol, etc.) may be used. In this case the water formed in the reaction is separated and this shifts the reaction equation towards the formation of the Schiff-base. This product is then reduced into the corresponding compound of the formula I. One may also proceed by carrying out condensation and reduction simultaneously. Reduction is preferably accomplished with the aid of nascent hydrogen.

According to a further embodiment of method (a) a 2-furyl-acetone of the formula VI

  (VI)

is reacted with an amine of the formula V.

  (V)

with simultaneous or subsequent reduction. The reduction can be accomplished preferably with the aid of nascent hydrogen.

According to a further embodiment of method (a) a compound of the formula VII

  (VII)

(wherein X is halogen or a sulfonic acid radical, e.g. an alkylsulfonyloxy or arylsulfonyloxy group, such as chlorine, bromine, methanesulfonyloxy, phenylsulfonyloxy or p-toluenesulfonyloxy) is reacted with an amine of the formula V. The reaction can be carried out in the presence or absence of a solvent. As reaction medium hydrocarbons (e.g. benzene and its homologues, petrol etc.) alcohols or ketones may be used. An excess of the amine component can also serve as the reacting medium. The reaction is preferably accomplished in the presence of an acid binding agent. For this purpose organic or inorganic bases or an excess of the amine of the formula V may be used. The reaction can be carried out at a temperature between 20° and 130° C. The recovery and purification of the product may be carried out by known physical methods (e.g. extraction, distillation, crystallization).

According to method (b) a compound of the formula IV is reacted with paraformaldehyde and acetylene. The reaction is carried out in an ether of high boiling point (e.g. butylether or dioxane) in the presence of cuprous acetylide. The reaction is performed preferably at a temperature of 80° to 150° C. One may proceed preferably by dissolving the compound of the formula IV in dioxane, adding cuprous acetylide or a compound capable of forming cuprous acetylide (e.g. cuprous — chloride) and introducing acetylene into the mixture under heating and stirring. The compound of the formula I may be isolated by methods known per se.

The propinyl group may also be formed by subsequent modification of a halogenopropenyl derivative. Thus one may proceed by reacting a compound of the formula IV with an 1,2-dihalogeno-alkene (e.g. 1,2-dibromo-propene) and splitting off hydrogen halide from the halogens-propenyl derivative thus obtained with an alkali hydroxide, alkaline earth metal hydroxide, or an organic base.

The compounds of the formula I thus obtained may be converted into a pharmaceutically acceptable acid addition salt formed with an inorganic or organic acid. The product may also be purified through the salts under utilising the fact that the salts are crystalline, readily crystallisable substances. After purification the base is set free from the salt by treatment with an alkali. For salt-formation hydrochloric acid, hydrobromic acid, sulfuric acid, phosphoric acid, maleic acid, lactic acid, citric acid, scorbic acid, etc. may be used.

Compounds of the formula I in which $R^1$ is an alkyl group contain a chiral carbon atom and may exist in racemic or optically active forms. The racemate may be subjected to resolution by conventional method. The optically active compound of the formula I may also be prepared by using an optically active amine of the formula IV in the reactions (a) and (b).

According to a further feature of the present invention there are provided pharmaceutical compositions comprising as active ingredient a compound of the formula I or its salt in admixture with suitable inert solid or liquid carriers or diluents. The compositions may be finished in solid (e.g. tablets, pills, coated pills, capsules, dragees, powder mixtures) or liquid (e.g. aqueous solution or suspension) forms. The compositions are suitable for oral, or parenteral administration. The compositions contain conventional carriers, e.g. talc, calcium carbonate, magnesium stearate, water, vaseline, polyalkylene glycols, etc. The compositions are prepared by methods of pharmaceutical industry known per se.

The N-methyl-N-[2-(furyl-2)-ethyl]-propynyl amine in an in vivo dose of 6.25 mg./kg. inhibits in the liver the oxidation of benzyl amine to an extent of 79% and the oxidation of thyramine only by 44%. In a dose of 5 mg./kg. N-methyl-N-[1-methyl-2-(furyl-2)-ethyl]propynyl amine inhibits in the brain the oxidation of benzylamine to an extent of 53% and that of 5-hydroxytryptamine only by 2%. On the other hand the known compound N,alpha-dimethyl-N-beta-phenyl-ethyl-N-propynyl amine shows in the same dose an inhibition of 80% of the oxidation of benzylamine in the brain, while the inhibition of the oxidation of 5-hydroxy-tryptamine is 15%. The said known phenyl derivative when administered in a dose of 10 mg/kg. inhibits the oxidation of benzylamine in the liver by 78%, and the oxidation of 5-hydroxy tryptamine by 56%. The above data show that the compounds of the formula I exhibit a more selective monoaminooxidase inhibiting effect, than the known phenyl derivatives. According to in vitro tests the selectivity is more pronounced.

The reserpine depression antagonizing antidepressive effect of the compounds of the formula I is significantly stronger than that of the phenyl analogues.

The toxicity of the compounds of the formula I is smaller, than that of the known phenyl derivatives, and therefore the new compounds of the present invention possess a more advantageous therapeutic index and a broader spectrum of activity.

Further details of the present invention are to be found in the Examples without limiting the scope of our invention to the Examples.

EXAMPLE 1

7.9 g. (0.0568 moles) of N-methyl-N-[1-methyl-2-(furyl-2)-ethyl]-amine are dissolved in 142 ml. of toluene, whereupon at 45° to 50° C. 6.7 g. (0.0568 moles) of propargyl bromide and 11.4 ml. of a 5 N aqueous sodium hydroxide solution are added at the same time under stirring. The reaction mixture is refluxed under stirring for 3 hours. After cooling 14.8 ml. of a 10 N sodium hydroxide solution are added and the phases are separated. The aqueous layer is extracted twice with benzene, whereupon the benzene and toluene solutions are united, dried over anhydrous potassium carbonate and evaporated. The residue is dissolved in 50 ml. of benzene and refluxed with 6 g. of acetic anhydride for an hour. After cooling the solution is washed with a 20% sodium carbonate solution until the evolution of carbon dioxide ceases. The mixture is washed with water and extracted with 5% hydrochloric acid at 0° C. The hydrochloric acid solutions are united, the mixture is allowed to stand at a temperature below 10° C., and made alkaline. The separated oil is extracted with ether, the ether extract is dried over potassium carbonate and evaporated. On subjecting the residue to vacuum destillation 6.5 g. of N-methyl-N-[1-methyl-2-(furyl-2)-ethyl]-propynyl-amine are obtained. Bp.: 115°–117° C./20 Hgmm; $n_D^{20} = 1.4922$.

EXAMPLE 2

The process according to Example 1 is carried out except that 12.5 g. of N-methyl-N-2-(furyl-2)-ethyl amine 11.9 g. (0.1 mole) of propargyl bromide are reacted in 70 ml. of toluene and 20 ml. of a 5 N sodium hydroxide solution. Thus 11.2 g. of N-methyl-N-[2-(furyl-2)-ethyl]-propynyl amine are obtained. Bp.: 105°–106° C./20 Hgmm; $n_D^{20} = 1.4891$. The melting point of the hydrochloride amounts to 106°–108° C. (from a mixture of ethanol and ether).

EXAMPLE 3

To 13.9 g. (0.1 mole) of N-methyl-N-[1-methyl-2-(furyl-2)-ethyl]amine 10 g. (0.05 moles) of 1,2-dibromo-propene are added dropwise, the reaction mixture is heated at 100° C. for 7 hours, whereupon it is cooled to room temperature and dissolved in 5% hydrochloric acid. The acidic solution is extracted with ether and made alkaline with 40% sodium hydroxide. The precipitated oil is extracted with ether, the extract is dried and evaporated. To the residual brown oil 60 ml. of 40% sodium hydroxide and 30 ml. of benzoyl chloride are added parallelly dropwise within 30–45 minutes in order to benzoylate the unreacted N-methyl-N-[methyl-2-(furyl-2)-ethyl] amine. During the addition the temperature of the reaction mixture rises to 50°–60° C. The addition having been completed the reaction mixture is stirred at this temperature for an hour, whereupon it is cooled to room temperature and benzene is added. The mixture is shaken and the benzene phase is separated and extracted with 5% hydrochloric acid. The N-methyl-N-[1-methyl-2-(furyl-2)-ethyl]-N-2-bromopropenyl amine dissolves in the acidic phase, while the N-methyl-N-[1-methyl-2-(furyl-2)-ethyl]-benzoyl amine remains in the benzene solution. The hydrochloric acid layer is made alkaline, the precipitated N-methyl-N-[1-methyl-2-(furyl-2)-ethyl]-N-2-bromo-propenyl amine is extracted with benzene, dried and evaporated. The residue is distilled off in vacuo. Thus 7.1 g. of N-Methyl-N-[1-methyl-2-(furyl-2)-ethyl]-N-2-bromo-propenyl amine are obtained. The product is dissolved in 100 ml. of ethanol and 14 ml. of an 50% aqueous potassium hydroxide solution are added. The reaction mixture is refluxed for 16 hours, whereupon the ethanol is distilled off and the residue is admixed with water and extracted with benzene. The benzene solution is dried over anhydrous potassium carbonate and evaporated. The residue is distilled off in vacuo. Thus 4.9 g. of N-methyl-N-[1-methyl-2-(2-furyl)-ethyl]-propynyl amine are obtained. Bp.: 114°–115° C./20 Hgmm; $n_D^{20} = 1.4915$.

EXAMPLE 4

12.5 g. (0.1 mole) of N-methyl-N-2-(2-furyl)-ethyl amine are reacted with 10 g. (0.05 moles) of 1,2-dibromo-propene according to Example 3. Thus 7.6 g. of N-methyl-N-[2-(2-furyl)-ethyl]-2-bromo-propenyl amine are obtained, which is reacted with 14 ml. of 50% aqueous potassium hydroxide in 100 ml. of ethanol under heating to boiling as described in Example 3. Thus 5.1 g. of N-methyl-N-[2-(2-furyl)-ethyl]-propynyl amine are obtained. Bp.: 105°–106° C./20 Hgmm; $n_D^{20} = 1.4890$. The melting point of the hydrochloride amounts to 107°–108° C. (from a mixture of ethanol and ether).

EXAMPLE 5

12.4 g. (0.1 mole) of 2-furyl-acetone are dissolved in 100 ml. of ethanol, whereupon 7.25 g. (0.105 moles) of methyl-propinyl amine are added. 3.5 g. of aluminium foiles are degressed with ethanol and thereafter activated with a solution of 1 g. of mercuric chloride and 15 g. of sodium chloride in 30 ml. of water. The activating solution is decanted after 6–8 minutes and the activated aluminum foils are washed with cold water and added to the alcoholic solution previously prepared under stirring. An exothermic reaction takes place and the temperature is kept at 15° to 30° C. by cooling. The reaction mixture is stirred for 24 hours, whereupon 30 ml. of 40% sodium hydroxide are added. The two phases are separated, the lower aqueous phase is extracted three-times with benzene. The benzene solutions are united with the previously separated alcoholic phase and evaporated. The residue consists of an organic oily layer and an aqueous phase which is extracted with benzene and the benzene solution is dried over potassium carbonate. The benzene is removed and the residue is distilled off in vacuo. Thus 6.7 g. of N-methyl-N-[1-methyl-2-(2-furyl)-ethyl]-propynyl amine are obtained. BP.: 113°–115° C./20 Hgmm; $n_D^{20} = 1.4905$.

EXAMPLE 6

13.9 g. (0.1 mole) of N-methyl-N-[1-methyl-2-(2-furyl)-ethyl] amine and 7 g. (0.184 moles) of propargyl aldehyde are reacted in 100 ml. of ethanol in the presence of 3.5 g. of aluminium foils as described in Example 5. Thus 6.1 g. of N-methyl-N-[1-methyl-2-(2-furyl)- ethyl]-propynyl amine are obtained. Bp.: 114°–115° C./20 Hgmm; $n_D^{20} = 1.4910$.

EXAMPLE 7

13.9 g. (0.1 mole) of N-methyl-N-[1-methyl-2-(2-furyl)-ethyl] amine are dissolved in 80 ml. of dioxane, whereupon 6 g. of paraformaldehyde and 1 g. of cuprous chloride are added and gaseous acetylene is introduced into the solution at 80° C. under stirring for 30 hours. The reaction mixture is filtered and the filtrate is evaporated. The residue is dissolved in benzene, the benzene solution is washed with water, dried over potassium carbonate and evaporated. The residue is distilled off in vacuo. Thus 6.8 g. of N-methyl-N-[1-methyl-2-(2-furyl)-ethyl]-propynyl amine are obtained. Bp.: 114°–116° C./20 Hgmm; $n_D^{20} = 1.4910$.

EXAMPLE 8

12.8 g. (0.1 mole) of 1-methyl-2-(2-furyl-ethyl)chloride and 15 g. (0.208 moles) of methyl-propinyl amine are heated in a sealed bomb tube at 70° to 80° C. for 4 hours. The reaction mixture is cooled, 30 ml. of 40% sodium hydroxide are added and the mixture is extracted with benzene. The benzene solution is dried, evaporated and the residue is distilled off in vacuo. Thus 9.8 g. of N-methyl-N-[1-methyl-2-(2-furyl)-ethyl]-propynyl amine are obtained. Bp.: 113°–115° C./20 Hgmm; $n_D^{20} = 1.4904$.

EXAMPLE 9

11.45 g. (0.1 mole) of 2-furyl-ethyl-chloride are reacted with 15 g. (0.208 moles) of methyl-propinyl amine according to the method described in Example 8. Thus 8.8 g. of N-methyl-N-[2-(furyl-2)-ethyl]-propynyl amine are obtained. Bp.: 104°–105° C./20 Hgmm; $n_D^{20} = 1.4868$.

What we claim is:

1. A racemic or optically active compound of the formula

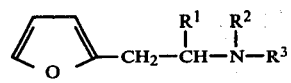

or a pharmaceutically effective salt thereof wherein $R^1$ and $R^2$ are lower alkyl and $R^3$ is halogenoalkenyl with 2 or 3 carbon atoms and chloro or bromo as the halogen, or propynyl.

2. A racemic or optically active N-methyl-N-[1-methyl-2-(2-furyl)-ethyl]-propynyl-amine or a pharmaceutically effective salt thereof.

3. A racemic or optically active N-methyl-N-[2-(2-furyl)-ethyl]-propynyl-amine or a pharmaceutically effective salt thereof.

4. The compound defined in claim 1 wherein $R^3$ is bromopropenyl.

5. A hydrochloride salt of a compound as defined in claim 1.

6. A pharmaceutical composition comprising as active ingredient a pharmaceutically effective amount of racemic or optically active compound as defined in claim 1 or a salt thereof in admixture with a suitable inert solid or liquid pharmaceutically acceptable carrier or diluent.

7. The pharmaceutical composition defined in claim 6 in the form of tablets, pills, coated pills, dragees, capsules, powder mixtures or solution.

8. Method for the inhibition of monoamine oxidase in subjects requiring such treatment which comprises the step of administering an effective amount of a composition according to claim 6 to such subjects.

* * * * *

UNITED STATES PATENT AND TRADEMARK OFFICE
CERTIFICATE OF CORRECTION

PATENT NO. : 4,162,327
DATED : 24 July 1979
INVENTOR(S) : KNOLL et al.

It is certified that error appears in the above—identified patent and that said Letters Patent are hereby corrected as shown below:

Claim 1, line 5 (counting the formula as line 3), Colum 8, line 10, the text should read:

-- and $R^2$ are hydrogen or lower alkyl and $R^3$ is halogenoalkyl with --

Signed and Sealed this

Eighth Day of April 1980

[SEAL]

Attest:

Attesting Officer

SIDNEY A. DIAMOND

Commissioner of Patents and Trademarks